US010586411B2

(12) United States Patent
Zurkuhlen et al.

(10) Patent No.: US 10,586,411 B2
(45) Date of Patent: Mar. 10, 2020

(54) ORDERING AND DELIVERY CUBICLE SYSTEM

(71) Applicant: Chip Chop Holdings, Inc., New York, NY (US)

(72) Inventors: Peter Zurkuhlen, New York, NY (US); David Cowan, New York, NY (US)

(73) Assignee: Chip Chop Holdings, Inc., New York, NY (US)

( * ) Notice: Subject to any disclaimer, the term of this patent is extended or adjusted under 35 U.S.C. 154(b) by 0 days.

(21) Appl. No.: 16/002,830

(22) Filed: Jun. 7, 2018

(65) Prior Publication Data
US 2018/0357843 A1 Dec. 13, 2018

Related U.S. Application Data

(60) Provisional application No. 62/517,347, filed on Jun. 9, 2017.

(51) Int. Cl.
*B60P 3/025* (2006.01)
*G06K 7/10* (2006.01)
(Continued)

(52) U.S. Cl.
CPC ............ *G07C 9/00111* (2013.01); *A61L 2/10* (2013.01); *B60P 3/0257* (2013.01); *G06Q 10/0633* (2013.01); *G07C 9/00134* (2013.01); *G07C 9/00896* (2013.01); *G07C 9/00904* (2013.01); *G07F 7/00* (2013.01); *G07F 11/002* (2013.01); *G07F 17/0071* (2013.01); *G07F 17/0078* (2013.01); *A61L 2202/14* (2013.01); *A61L 2202/23* (2013.01); *G07C 9/00309* (2013.01);
(Continued)

(58) Field of Classification Search
CPC .... G06Q 30/04; G06Q 50/12; G06Q 10/0633; G07C 2009/00277; G07C 2009/00349; G07C 2009/00769; G07C 9/00166; G07C 9/00571; G07C 9/00904; G07C 9/00912; G07C 2009/0092; G07C 9/00896; G07C 9/00111; G07C 9/00309; G07F 11/002; H04W 4/80; A61L 2202/14; A61L 2202/23; A61L 2/10; B65D 81/2076; H04L 67/1097; H04L 67/12; H04L 67/42
See application file for complete search history.

(56) References Cited

U.S. PATENT DOCUMENTS 8,261,980 B1 * 9/2012 Scutellaro .............. G06Q 50/12
235/383
2015/0356801 A1 * 12/2015 Nitu .................... G07C 9/00912
340/5.61
(Continued)

*Primary Examiner* — Dionne Pendleton
(74) *Attorney, Agent, or Firm* — Lowenstein Sandler LLP

(57) ABSTRACT

Embodiments of the disclosure are directed to an online ordering and delivery cubicle system. In one embodiment, a device is provided. The device includes a cubicle comprising a first opening and a second opening, and a cavity disposed therein. The first opening is opposite the second opening and the second opening is adapted to receive an item to be disposed into the cavity. A sensor coupled to the cubicle detects a state of the item with respect to the cavity. The device further includes an access assembly coupled to the first opening and the sensor. The access assembly is adapted to wirelessly activate to provide authenticated access via the first opening to the item in the cavity based on the state of the item.

20 Claims, 7 Drawing Sheets

(51) Int. Cl.
*G07F 9/00* (2006.01)
*G07C 9/00* (2020.01)
*A61L 2/10* (2006.01)
*G06Q 10/06* (2012.01)
*G07F 7/00* (2006.01)
*G07F 11/00* (2006.01)
*G07F 17/00* (2006.01)

(52) U.S. Cl.
CPC ............... *G07C 2009/0092* (2013.01); *G07C 2009/00769* (2013.01)

(56) References Cited

U.S. PATENT DOCUMENTS

| | | | |
|---|---|---|---|
| 2017/0011442 A1* | 1/2017 | Hu | G06Q 30/0621 |
| 2017/0096279 A1* | 4/2017 | Campalans | H04L 67/42 |
| 2019/0035044 A1* | 1/2019 | Ferguson | G06K 9/00201 |
| 2019/0082829 A1* | 3/2019 | Shoenfeld | A47B 67/02 |
| 2019/0122167 A1* | 4/2019 | Bashkin | G06Q 10/087 |
| 2019/0270398 A1* | 9/2019 | Goldberg | G06Q 10/08355 |

\* cited by examiner

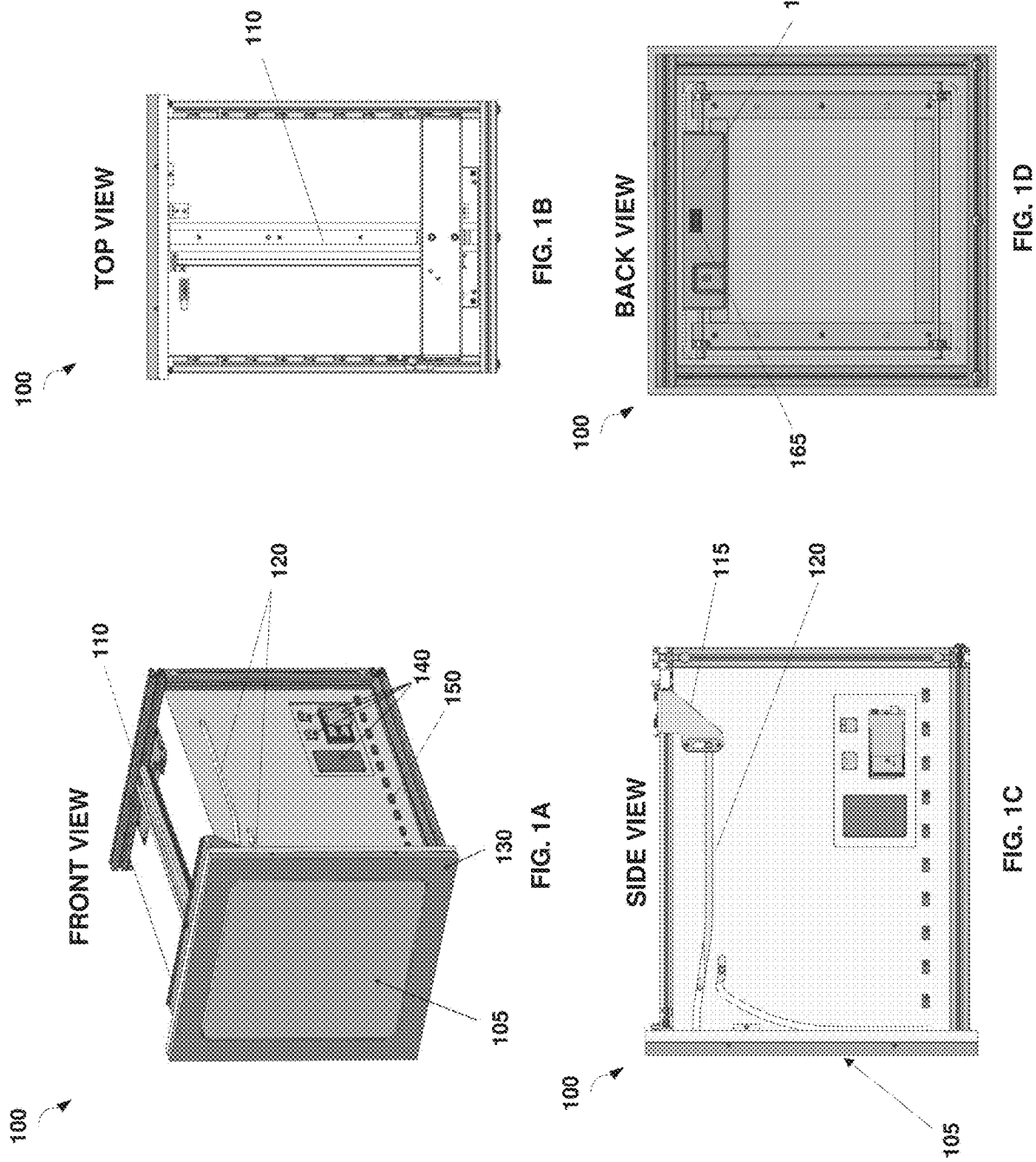

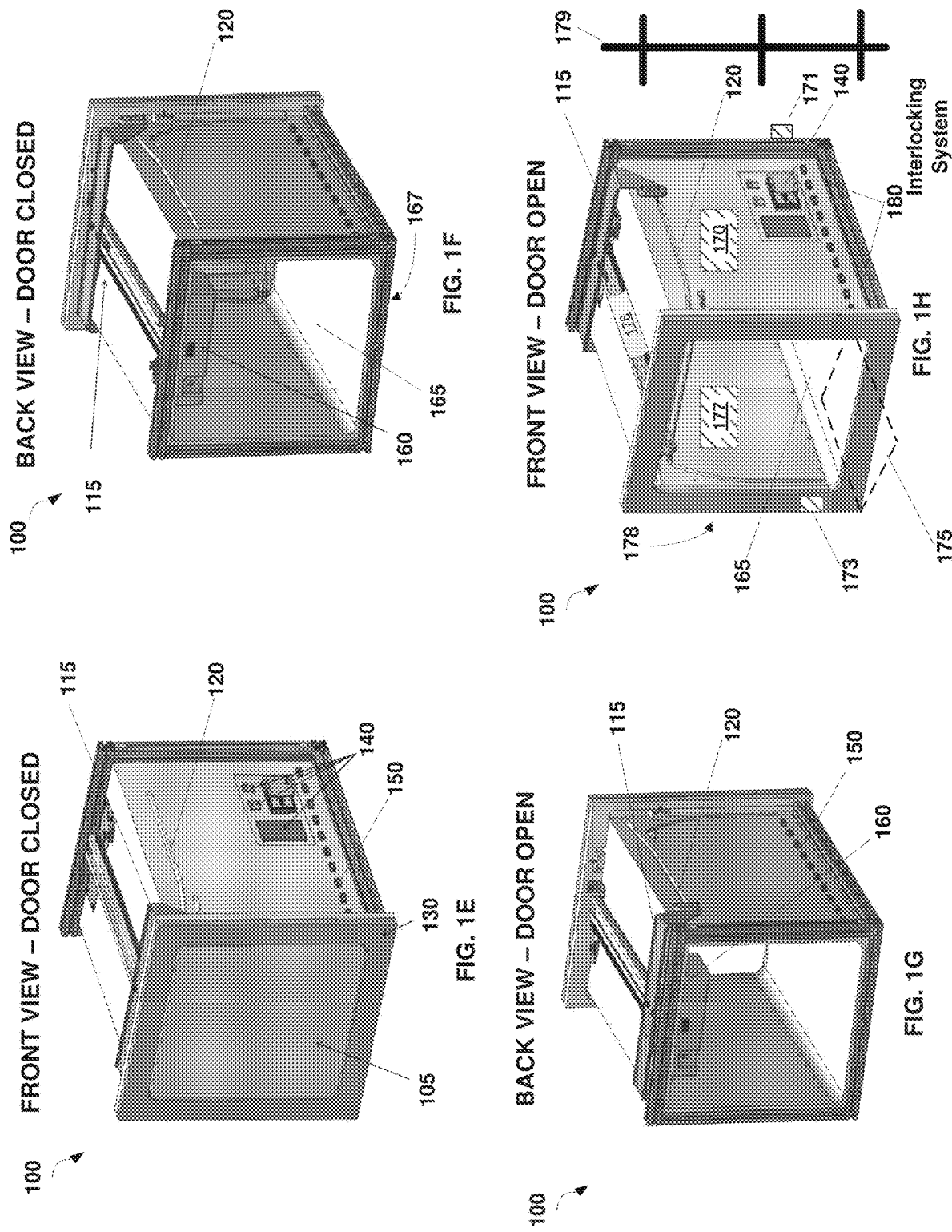

ORDERING AND DELIVERY CUBICLE SYSTEM

CROSS-REFERENCE TO RELATED APPLICATION

This application claims the benefit of priority from U.S. Provisional Application No. 62/517,347, filed Jun. 9, 2017, the entirety of which is incorporated herein by reference.

TECHNICAL FIELD

Embodiments of the disclosure relate generally to computer-based order processing systems, and more specifically, but without limitation, to an ordering and delivery cubicle system.

BACKGROUND

Businesses often have high-labor costs for employees whose job responsibilities include taking orders from customers and inputting those orders into an order-processing system. This not only means that businesses have to pay for employees to handle the mundane task of processing orders, but the employees also have to be trained to use the business's specific order-processing system. Advances in electronic and computer systems have improved the order-input process for these employees, but most of these systems still utilize employees to operate these systems.

BRIEF DESCRIPTION OF THE DRAWINGS

The disclosure is illustrated by way of example, and not by way of limitation, and will become apparent upon consideration of the following detailed description, taken in conjunction with the accompanying drawings, in which like reference characters refer to like parts throughout, and in which:

FIGS. 1A-1H are perspective views of an exemplary cubby device in accordance with embodiments of the disclosure.

DETAILED DESCRIPTION

Figure 2:
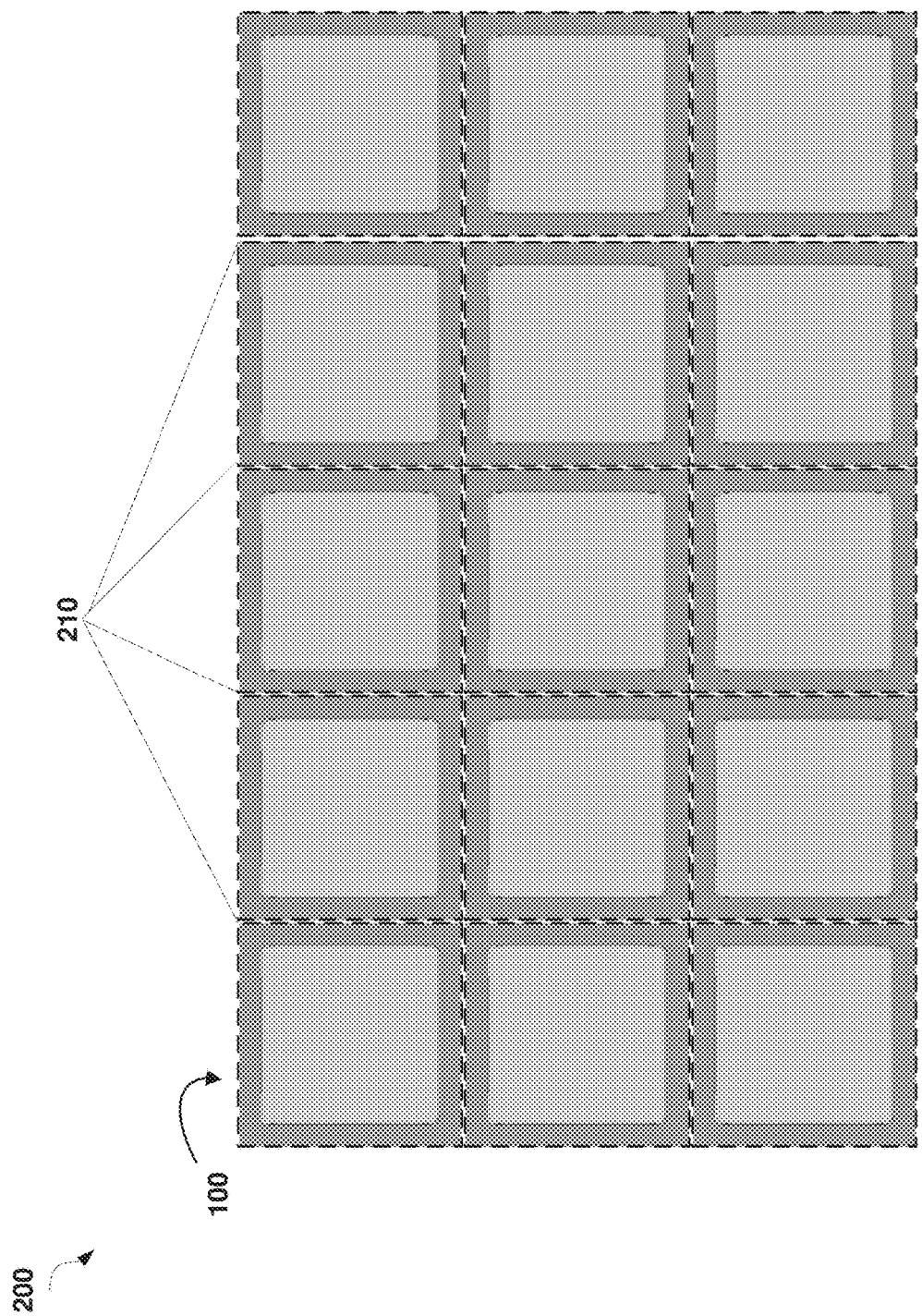
FIG. 2 is a block diagram illustrating a group of cubbies including the cubby device of FIGS. 1A-1G in accordance with embodiments of the disclosure.

Aspects and implementations of the disclosure are directed to an online ordering and delivery cubicle (hereinafter referred to as "cubby") system. It is contemplated that the systems and methods described herein may facilitate and improve the efficiency of a "take-out" ordering process used in particular businesses. However, so as to illustrate the functionality and corresponding processing of the ordering and delivery cubby system, and not by way of limitation, the particular business described herein is a restaurant type business. Implementations of the ordering and delivery cubby system described herein may be utilized to provide products to customer in a variety of businesses, such as a pharmacy, big-box stores, stadiums/entertainment venues, drive-thru, movie theaters, etc.

With respect to a restaurant, a customer can place a take-out order at the restaurant (e.g., customer may call the restaurant to place an order, order online, etc.). An employee stationed inside the restaurant may receive and service the order, and, subsequently, the customer can go to the restaurant and pick up the order once it is ready. Typically, take-out ordering represents a large portion of the restaurant industry in terms of dollars.

Unfortunately, the restaurant industry is typically managed in such a way as to diminish the potential revenue gains that can be achieved. For example, most restaurants do not have a dedicated system or staff for handling take-out orders. As a result, whichever employee is handling a customer's call is likely being distracted from his or her normal job. Moreover, the restaurant can often be busy, noisy, etc., which hinders communication of the take-out order between the customer and restaurant employee. Furthermore, the configuration and capabilities of the order entry/pick-up and telephony systems within a restaurant are typically not up to standard for order-taking activities. This can result in a difficult, inconsistent, or unsatisfying ordering experience, long pick-up lines, incorrect orders, long hold times, dropped calls, and the like.

Implementations of the disclosure address the above-mentioned and other deficiencies in order processing technologies by providing a system that can streamline the process of ordering and picking up items (e.g., "take-out" food) which, in turn, mitigates or otherwise eliminates any unnecessary human interactions. In some implementations, the system may include a cubby device, a scanning station coupled to the cubby device, and a mobile device (e.g., smartphone, tablet, etc.) of a customer that is in communication with the scanning station to activate the cubby device.

In operation, the customer may place their order utilizing an application (such as a third-party application) executed on the customer's device (e.g., mobile device, tablet device, desktop computer, etc.). In one implementation, the application may be downloaded to the customer's device. The order is sent to the restaurant, where it is prepared on the back-end, for example, by a prep chef. The prep chef may pass the prepared order to a runner (e.g., an employee whose main responsibility includes bring items, such as food, from a kitchen to customers) in the back, who can put the order in one of a number of the cubbies stationed at the restaurant. The runner then scans a unique identifier, such as a QR code, on a reader device on the back end which is electronically coupled to the cubbies, so that the cubby system recognizes that same unique identifier on the front end when the customer scans it. When the customer arrives at the restaurant to pick up the order, they can proceed to a scanning station.

At the scanning station, the user may be provided with authenticated access to the particular cubby associated with the user's order. To provide authenticated access to the items within the cubby, the scanning station (and/or cubby) is configured to receive input from an authorized user to prevent unauthorized user access to an interior cavity of the cubby. For example, the scanning station may receive an indication that an identifier (e.g., Quick Response (QR) code), Universal Product Code (UPC) code, etc.) is provided on a display of the scanning station and/or at the cubby. The customer can then use their mobile device to scan the provided identifier code to gain access to the item in the cubby. For example, the scanning station compares a first identifier associated with the item that was entered by the runner with the second identifier presented by the user device. If the identifiers match, the scanning station activates the cubby to identify and provide the customer access to their order. In alternative implementations, the scanning station may detect that the customer's mobile device is in front of and/or near the scanning station using a wireless communication protocol, for example, near-field communication (NFC), Bluetooth, Wifi, Beacon device, etc. The scanning station identifies which cubby the customer is to go to pick up the order. In one implementation, the cubby containing the customer's food may be illuminated per instructions sent from the scanning station. The illuminated cubby can be opened, for example, manually or via a wireless signal from the customer's mobile device. Then, the customer can take the food out and leave with the order. The cubby ultimately closes, e.g., once the sensors detect that the order is retrieved or otherwise removed from inside the cubby.

FIGS. 1A-1H are perspective views of an exemplary cubby device 100 in accordance with embodiments of the disclosure. In the example, the cubby device 100 may be a structure of a particular shape, such as a cube shape, that includes a cavity (opening) to allow items to be rested or stored within the cubby. In some embodiments, the cavity of the cubby device 100 includes a first (front) opening (not shown; that is opposite a second (rear) opening (not shown). The second opening is adapted to receive an item to be disposed into the cavity. The item can later be retrieved via the first opening by the customer. In alternative implementations, other shapes are possible. In FIG. 1A, a front view of the cubby device 100 is shown. FIG. 1B depicts a top view of the cubby device 100. FIG. 1C depicts a side view of the cubby device 100. FIG. 1D depicts a back view of the cubby device 100. With respect to the back view in FIG. 1D, the cubby device 100 is shown without a back covering structure. In alternative implementations, the cubby device 100 may include a back covering structure.

In some implementations, the body of the cubby device 100 may be comprised of various materials, such as metal, plastic, PVC, etc., and be constructed in various sizes. In some implementations, the cubby device 100 may include several components, such as a door assembly 105, a access assembly 110 (such as a pulley system) to actuate (e.g., open/close) the door assembly via a rail 120, a LED faceplate 130, electronic control components 140, various sensors (e.g., a beam break sensor 150) to detect the state, such as the presence or removal) of an object (e.g., food/drink) in the cubby, power source component to power parts of the cubby, as well as other components. The door assembly 105 may be made of a flexible material (such a type of metal or plastic) that can bend as the door assembly is being opened and/or closed. In some implementations, the door assembly 105 may include several ridges that help facilitate bending of the door assembly during opening and closing.

To actuate (e.g., open/close) the door assembly, the control processing devices 140 may receive a signal (e.g., from a scanning device such as the scanning station described above) that activates the access assembly 110. As shown in FIG. 1C, the access assembly 100 may include an actuator 115 coupled to door assembly 105 that moves along a length of the cubby device 100 from front to back and back to front via rails 120. As shown in FIG. 1D, the access assembly 110 may be coupled to a motor component 160 that allows the actuator 115 of the access assembly 110 to be pulled along a length on the cubby device 100. When the actuator 115 actuates or otherwise raises the door assembly 105 open, the door assembly 105 may move into the cubby device 100 to expose the cavity disposed therein. Alternatively, when the actuator 115 actuates or otherwise lowers the door assembly 105 closed, the door assembly 105 may move out of the cubby device 100 to cover the cavity within the cubby. In this position, the actuator 115 performs as a lock to hold the door assembly 105 closed until the access assembly 110 activates the door to open. In some implementations, the cubby device 100 may include light 165 or another type of indicator on the back (or in other positions) of the cubby. For example, when the runner on the back end scans the identifier at a reader device 165 electronically coupled to the cubby (such as on the cubby or at the scanning station), the light 165 on the back of one of the vacant cubbies illuminates, so that they know which cubby the item is to be placed therein.

Turning to FIG. 1E, a front view of the cubby device 100 is shown with the door assembly closed. For example, the actuator 115 of access assembly 110 may be in a first position that is situated at the front of the cubby. With respect to FIG. 1F, a back view of the cubby device 100 is shown with the door assembly closed. As shown in FIG. 1F, items (e.g., food/beverage items) can be placed into cavity 165 through an opening 167 at the rear of the cubby device 100. Turning to FIG. 1G, the back view of the cubby device 100 is shown with the door assembly opened. With respect to FIG. 1H, a front view of the cubby device 100 is shown with the door assembly opened. For example, the actuator 115 of access assembly 110 may be moved via rail 120 to a second position that is situated at the back of the cubby. As such, the actuator 115 may pull the door assembly open by moving the door assembly into the cubby device 100 using motor 160. Once the door assembly is opened, the items within the cavity 165 of the cubby 100 can be removed via another opening 178 at the front of the cubby 100. In this regard, the beam break sensors 150 may detect when the items have been removed, and, subsequently, send a signal to the electronic control components 140 of the cubby device 100 to close the door assembly. For example, the beam break sensor 150 may include one or more light beams that are projected across the interior of the cubby device 100. When the light beams are broken, this indicates that an item has been placed within the cubby. When the item is subsequently removed, the beam break sensor 150 may detect that the light beams are unbroken. In some implementations, the cubby 100 may be a programmable with a determined 'x' second delay to close the door assembly after the sensors detect that the items have been removed, so that the cubby 100 does not start closing on someone the second that an item is no longer detected within the cubby 100 by the beam break sensors 150.

As shown in FIG. 1H, the cubby device 100, in implementations, may be coupled to a heating/cooling component 170. For example, the heating/cooling component 170 may allow the cubby to keep certain items at a determined temperature to ensure a quality of the item within the cubby. In some implementations, the cubby device 100 may include a reader 171 that allows a runner to scan an identifier (e.g., QR code) that is stored in a data structure (e.g., a database table) on a back end server, so that the cubby device 100 recognizes that same identifier on the front end when the customer scans the identifier on a second reader 173 on the front of the cubby. In other implementations, the readers 171, 173 may not be on the cubby device 100, but rather located at one or more scanning stations (not shown) associated with the cubby device 100. In some implementations, the cubby device 100 may include a mechanical tray 175 on the bottom/floor of the cubby's interior that slides out when the cubby door assembly opens, bringing the food/item closer to the customer. For example, such a mechanical tray 175 that slides may be utilized in a drive-thru location, where a car may not be able to get as close to the cubby as someone on foot. In another implementation, the cubby device 100 may include a light system 177 (e.g., a ultraviolet (UV) light system) within the cubby to periodically sanitize (e.g., kill certain bacteria) the interior of the cubby device 100 after the items have been retrieved by the customer. For example, the light system 177 may include germicidal ultra violet lamps that are integrated into an interior cavity of the cubby device 100. This light system 177 may be integrated in such a way to ensure that the entire interior surface interior of the cubby device 100 is sanitized after seconds of exposure to the light emissions from the light system 177. These types of lamps may be fluorescent, but LED or some other technology may be utilized.

Alternate iteration of the door assembly for the cubby device 100 is that it may open out and up, as opposed to up-and-in like a garage door. For example, when triggered, the door assembly pushes straight out an inch or two, and then goes straight up so that nothing in the cubby device 100 gets interrupted or compromised by the door assembly sliding into the top. In another implementation, the cubby device 100 may include a type of alternate mechanical device 178 for the cubby 100 to operate without using electronics. For example, the mechanical device 178 may include a wax and spring system where the door assembly would be powered by a spring when opened and slowed down by some kind of wax.

In other implementations, the cubby device 100 may include an interlocking system 180 that allows a group of cubbies to be joined together to form a modular structural ordering and delivery system. In some implementations, the group cubbies may be mounted to a mechanical track system 179 such that they can move up, down, left, right (possible forward and backward) to adjust each cubbies height and general location. In this regard, there may be multiple scanning unit locations at different heights and a corresponding cubby may be moved to the height of a corresponding scanning unit that receives input from the customer. This may be particularly beneficial to increase access for people of various heights, people in wheelchairs, people in cars (where driver-side window heights differ dramatically), etc. Further features of the group of cubbies are depicted with respect to FIG. 2.

FIG. 2 is a block diagram illustrating a group of cubbies 200 including the cubby device 100 of FIGS. 1A-1G in accordance with embodiments of the disclosure. In this example, each of the cubbies 200 includes interlocking connectors 210 to attach (or secure) portions or other types of structural components of each of the cubbies together. In one implementation, the interlocking connectors 210 are the same as interlocking system 180 described with respect to FIG. 1. These interlocking connectors 210 can take various forms. For example, each cubby, such as cubby 100, may include interlocking connectors 210 that allow a portion of cubby 100 to slide into the attaching structural unit along the edge of a second cubby and thus prevents detachment between the two cubbies. In other implementations, interlocking connectors 210 may be connected together using other techniques.

In some implementations, the interlocking connectors 210 are made of a highly rigid material, such as plastic or metal, which can support the weight of the cube. In some implementations, interlocking connectors 210 allow for an assembly of the cubbies into an interlocking modular cube-like structure that forms horizontal and vertical arrays of cubbies.

Figure 3:
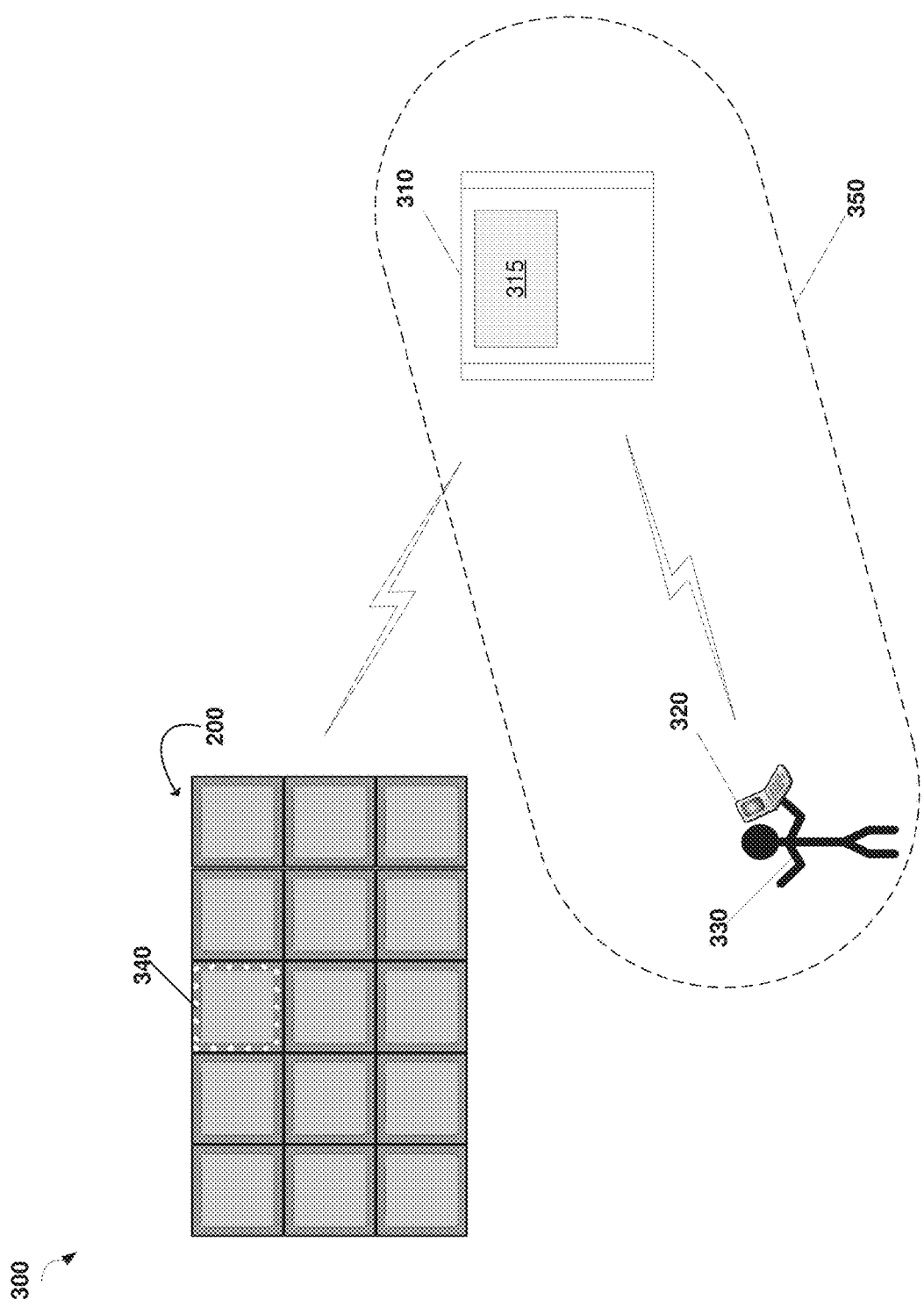
FIG. 3 is a block diagram illustrating a system in which embodiments of the disclosure may operate.

FIG. 3 is a block diagram illustrating a system 300 in which embodiments of the disclosure may operate. In this example, the system 300 includes the group of cubby devices 200 of FIG. 2, a scanning station 310 communicatively coupled to the cubbies, and a mobile device 320 (such as a smartphone/tablet) of a customer 330 that is in communication with the scanning station 310 to activate at least one cubby of the cubby devices 200. In some implementations, mobile device 320 may have stored thereon an application to facilitate different types of electronic communications between the mobile device 320 and system 300 via a network. In one implementation, the application may be installed and/or a service may be selected in order to obtain the benefits of the techniques described herein. In an implementation, the application may be downloaded onto the mobile device 320. For example, a user may elect to download the application from a service associated with an online server. The mobile device 320 may transmit a request for the application over a network, and, in response, receive the application from the service.

The customer 330 may use the application via their mobile device 320 to place an order for an item. For example, the customer 330 may place a take-out order for a food item from a restaurant associated with the application. The customer 330 may choose from various (food) items offer by the restaurant. Once the order is placed via the application on the mobile device 320, the order is transmitted to the restaurant via the application. When the order in received at the restaurant (e.g., via a corresponding business interface of the application), the order is prepared on the back-end, for example, by a prep chef. The prep chef may pass the prepared order to a runner in the back who places the order in one of the group of cubbies 200 stationed at the restaurant. In turn, the customer 330 may receive a notification via his or her mobile device 320 (e.g., via the application on the mobile device 320) that the order is ready for pick-up.

When the customer 330 arrives at the restaurant to pick up the order, they can proceed to the scanning station 310. The scanning station is adapted to activate at least one cubby of the cubby devices, such as the cubby devices 200 of FIG. 2, to provide the user with authenticated access to the item associated with their order. In order to provide authenticated access to the items within the cubby, the scanning station is configured to receive input from an authorized user to prevent unauthorized user access to the interior of the cubby. At the scanning station 310, the mobile device 320 is scanned using a display 315. In alternative implementations, the scanning station 310 may detect that the customer's mobile device 320 is in the restaurant or within a certain proximity or threshold range 350 and/or in front of the station. For example, the scanning station 310 may detect the customer's mobile device 320 by using a wireless communication protocol, for example, near-field communication (NFC), Bluetooth, Wifi, etc. The customer 330 then presents an identifier (e.g., a QR code) to the scanning station 310. When the scanning station 310 recognizes the identifier from the customer's mobile device 320 (or other form of presenting the code), the system 300 recognizes the identifier from when it was scanned by the runner on the back end. For example, the scanning station 310 compares the identifier associated with the item that was entered by the runner with the identifier presented by the user device. If the identifiers match, the scanning station 310 actuates the access assembly of the cubby to identify and provide the customer the order. The system 300, in embodiments, illuminates and opens the cubby that corresponds to the customer's order.

To illuminate and open the cubby, the scanning station 310 transmits a signal to the group of cubbies 200 to identify an association between a particular cubby and a user based on the item in the cubby. For example, the signal is used to identify the cubby with the item for pick up by the customer 330. In some embodiments, the scanning station 310 may send a signal to illuminate and open the cubby 340 for the customer. In some implementations, the LED faceplate (such as LED faceplate 130 of FIG. 1) of the cubby may display a user-perceivable signal, such as a particular color, pattern or other type of graphic that indicates to the customer that the item stored therein is ready for pick up. For example, the scanning station 310 may provide an indication via the display 315 to instruct the customer to proceed to the Green illuminated cubby to pick up his or her item. The illuminated cubby 340 can open (e.g., responsive to the signal sent from the scanning station 310) and, subsequently, the customer 330 can take the item out and leave with the order.

After the order is retrieved, the illuminated cubby 340 may automatically close. For example, the beam break sensors 150 of cubby 340 may detect when the items have been removed, and, subsequently, sends a signal to the electronic control components 140 of the cubby 340 to close the door assembly. Thereupon, the cubby 340 can be used by the restaurant to facilitate the ordering and delivery of the next customer's take-out items.

FIG. 4 is a flow diagram illustrating an embodiment of a method 400 in accordance with embodiments of the disclosure. The method 400 may be performed by processing logic that comprises hardware (e.g., circuitry, dedicated logic, programmable logic, microcode, etc.), software (e.g., instructions run on a processing device to perform hardware simulation), or a combination thereof.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art should understand and appreciate that the methods could alternatively be represented as a series of interrelated states via a state diagram or events. Additionally, it should be appreciated that the methods disclosed in this specification are capable of being stored on an article of manufacture to facilitate transporting and transferring such methods to computing devices. The term "article of manufacture," as used herein, is intended to encompass a computer program accessible from any computer-readable device or storage media. In one implementation, method 400 may be performed by system 300, as shown in FIG. 3.

Figure 4A:
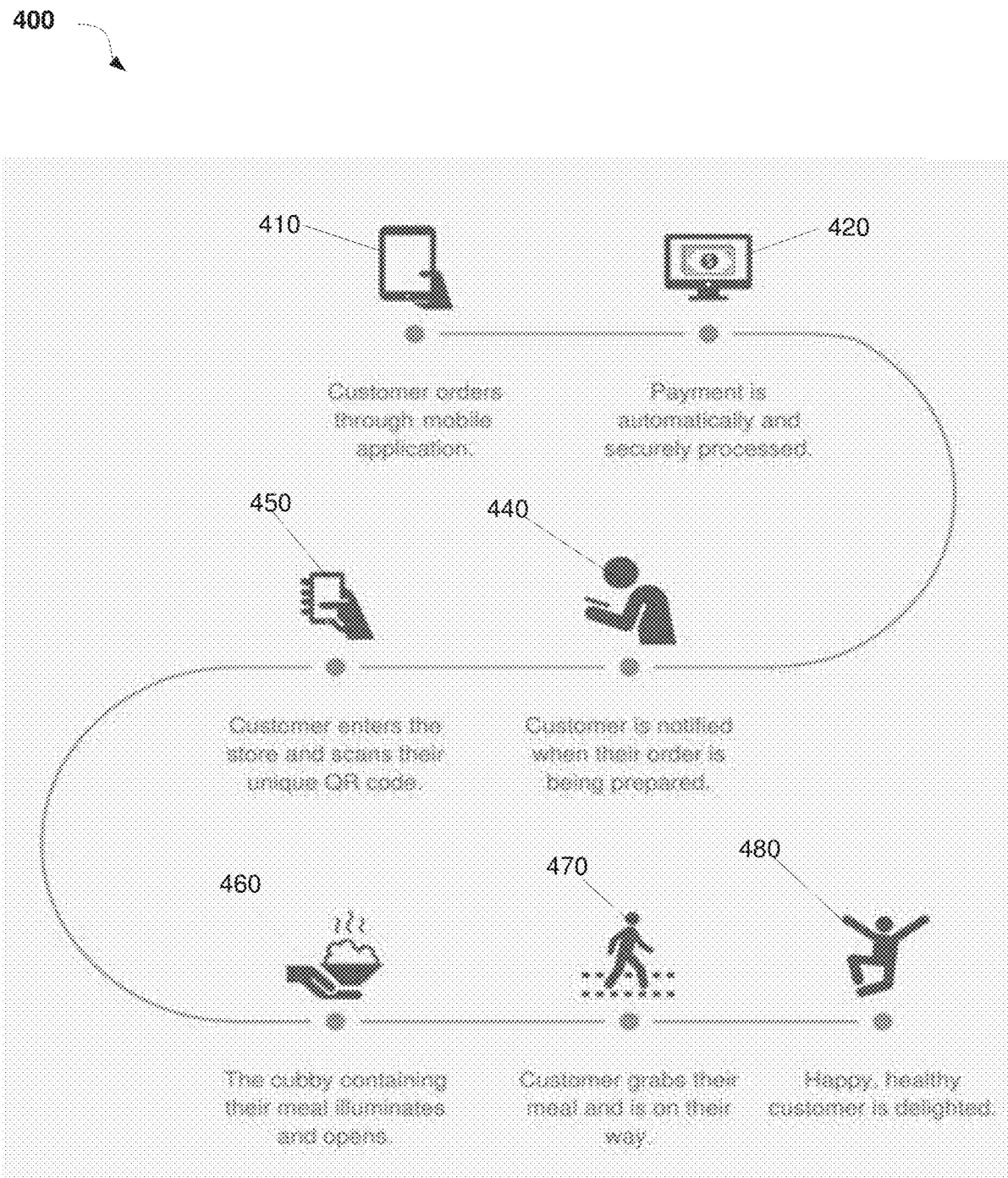
FIG. 4A is a flow diagram illustrating an embodiment of a method in accordance with embodiments of the disclosure.

As shown in FIG. 4A, method 400 begins at step 410 where a customer places an order through a mobile application, or through a desktop application, website, etc. For example, customer 330 may use a compatible application via their mobile device 320 to place an order for a take-out food item from a restaurant. At step 420, a payment is securely processed. For example, the payment for the item may be conducted by the mobile application or via a third-party application, such as Stripe® or PayPal®. At step 440, the customer 330 is notified when their order is being prepared and is ready for pick-up. For example, the customer 330 may be notified on their mobile device via text, push notification or other forms of communication. At step 450, the customer 330 enters the restaurant and scans his or her unique identifier, (e.g., QR code) at a scanning station 310. At step 460, the cubby 340 containing the customer's meal illuminates and opens. At step 470, the customer 330 takes their item and departs. At step 470, the customer 330 is delighted with their item and happily leaves the restaurant.

Figure 4B:
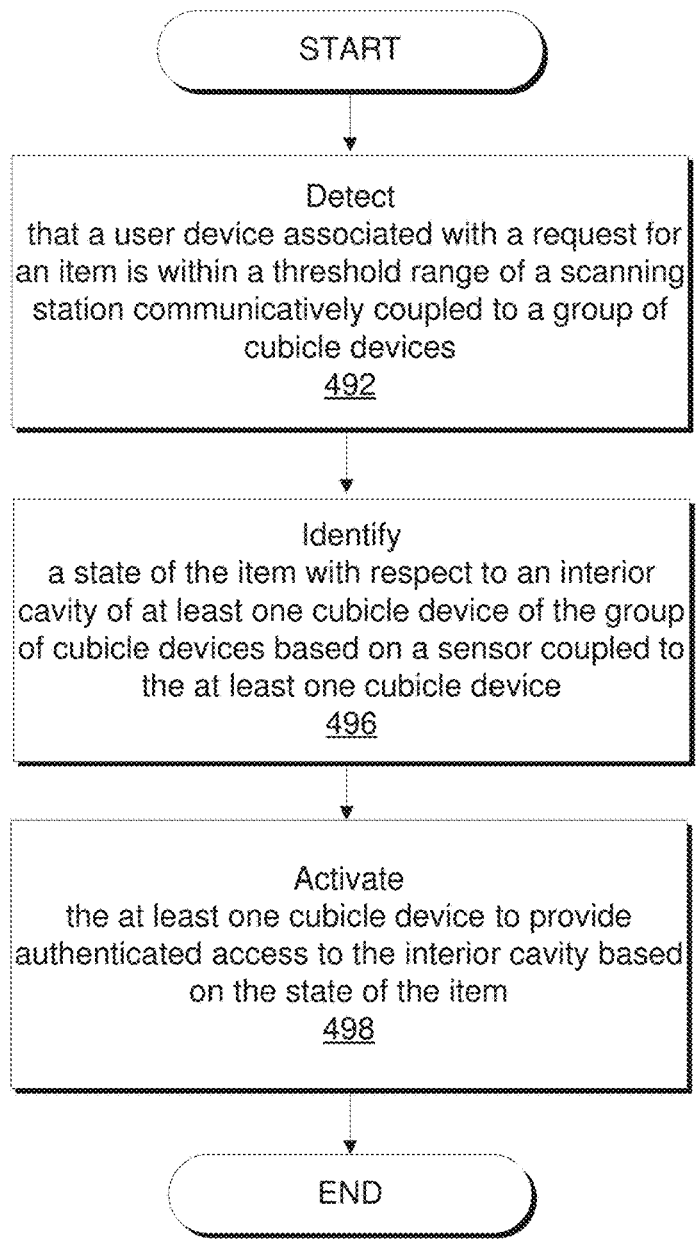
FIG. 4B is a flow diagram illustrating an embodiment of another method in accordance with embodiments of the disclosure.

FIG. 4B is a flow diagram illustrating an embodiment of another method 490 in accordance with embodiments of the disclosure. In one implementation, a processing device (e.g., scanning station 310) of FIG. 3 may perform method 490 to facilitate and improve the efficiency of a "take-out" ordering process as described herein. The method 490 may be performed by processing logic that may comprise hardware (circuitry, dedicated logic, etc.), software (such as is run on a general purpose computer system or a dedicated machine), or a combination of both. Alternatively, in some other implementations, one or more processors of the computer device executing the method may perform routines, subroutines, or operations may perform method 490 and each of its individual functions. It should be noted that blocks of method 490 depicted in FIG. 4B can be performed simultaneously or in a different order than that depicted.

Referring to FIG. 4B, in block 492, method 490 detects that a user device associated with a request for an item is within a threshold range of a scanning station coupled to a group of cubby devices. Each cubby device comprises a cubby having a first opening and a second opening, and a cavity disposed therein. In some embodiments, the first opening is opposite the second opening and the second opening is adapted to receive an item to be disposed into the cavity. A state of the item with respect to an interior cavity of at least one cubby device of the group of cubby devices is identified in block 496 based on a sensor coupled to the at least one cubby device. In some embodiments, the state of the item may include detecting a presence of the item in the cavity of the cubicle or detecting a removal of the item from the cavity of the cubicle. For example, a sensor of the cubby device may include one or more light beams that are projected across the interior of the cubby device. When the light beams are broken, this indicates that an item has been placed with the cubby. When the item is subsequently removed, the sensor may detect that the light beams are unbroken. Thereupon, the at least one cubby device is activated in block 498 to provide authenticated access to the interior cavity based on the state of the item.

Figure 5:
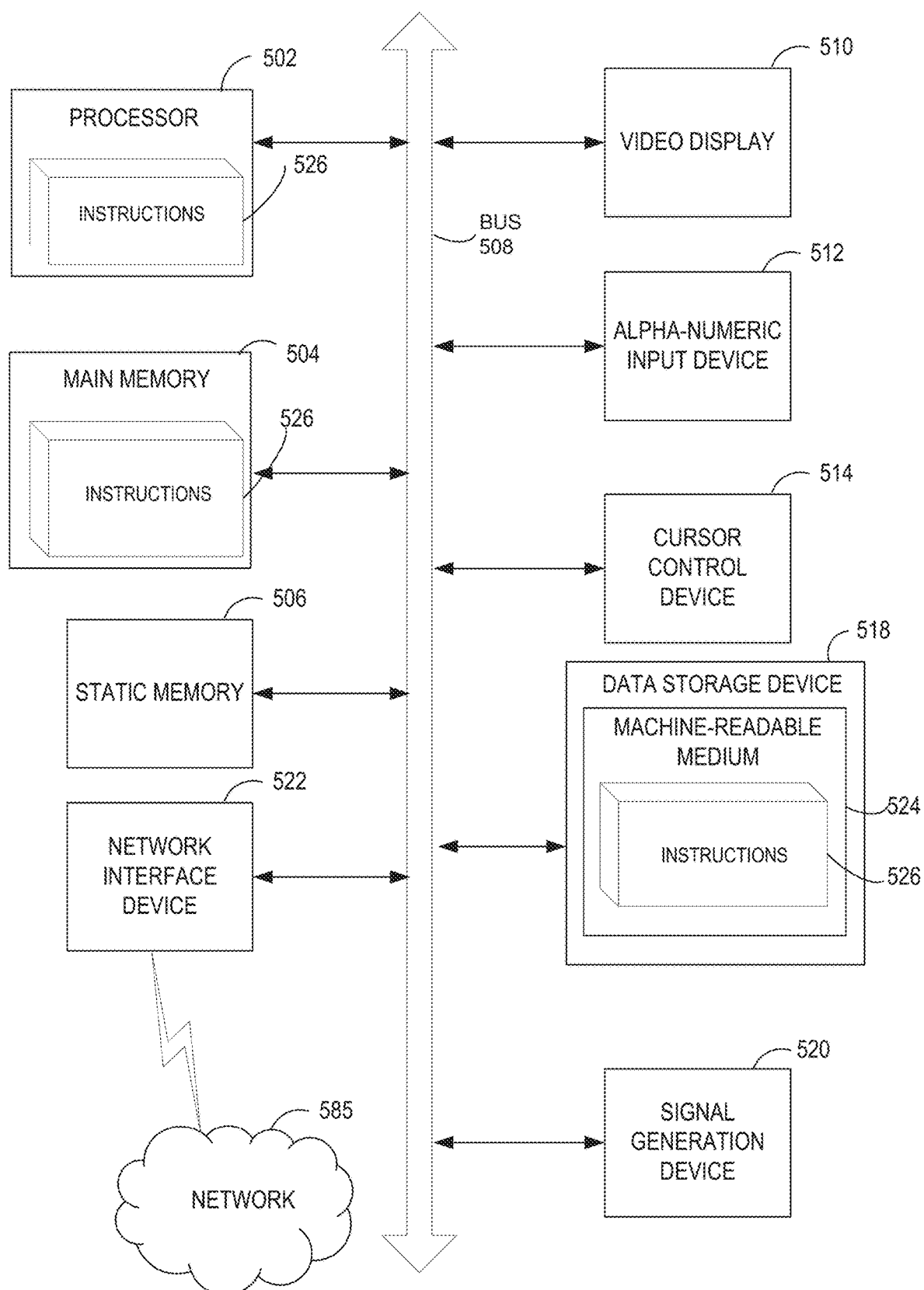
FIG. 5 illustrates a diagrammatic representation of a machine in the exemplary form of a computer system.

FIG. 5 illustrates a diagrammatic representation of a machine in the exemplary form of a computer system 500 within which a set of instructions, for causing the machine to perform any one or more of the methodologies discussed herein, may be executed. For example, aspect of computer system 500 may be part of cubby 100 described with respect to FIGS. 1A through 1H. In alternative implementations, the machine may be connected (e.g., networked) to other machines in a local area network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a personal digital assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 500 may be comprised of a processing device 502, a main memory 504 (e.g., read-only memory (ROM), flash memory, dynamic random access memory (DRAM) (such as synchronous DRAM (SDRAM) or Rambus DRAM (RDRAM), etc.), a static memory 506 (e.g., flash memory, static random access memory (SRAM), etc.), and a data storage device 516, which communicate with each other via a bus 508.

In a further aspect, the computer system 500 may include a processing device 502 (which may correspond to processing device 112), a volatile memory 504 (e.g., random access memory (RAM)), a nonvolatile memory 506 (e.g., read-only memory (ROM) or electrically-erasable programmable ROM (EEPROM)), and a data storage domain 516, which may communicate with each other via a bus 508.

Processing device 502 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. Processing device 502 is configured to execute processing logic (e.g., instructions 526) for performing the operations and steps discussed herein. For example, processing devices 502 may execute processing logic (e.g., instructions 526) to perform method 400 described with respect to FIG. 4.

Computer system 500 may further include a network interface device 522. Computer system 500 also may include a video display unit 510 (e.g., a liquid crystal display (LCD) or a cathode ray tube (CRT)), an alphanumeric input device 512 (e.g., a keyboard), a cursor control device 514 (e.g., a mouse), and a signal generation device 520 (e.g., a speaker, or a brail device or other forms of communication for people with blindness, deafness, or other types of limited abilities).

Data storage device 516 may include a machine-readable storage medium (or more specifically a computer-readable storage medium) 524 having one or more sets of instructions 526 embodying any one or more of the methodologies of functions described herein, including instructions 526 for the ordering and delivery cubby system.

Instructions 526 may also reside, completely or at least partially, within main memory 504 and/or within processing device 502 during execution thereof by computer system 500; main memory 504 and processing device 502 also constituting machine-readable storage media. The instructions 526 may further be transmitted or received over a network 525 via network interface device 522.

While a non-transitory machine-readable storage medium 524 is shown in an exemplary implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instruction for execution by the machine and that causes the machine to perform any one or more of the methodologies of the disclosure. The term "machine-readable storage medium" shall accordingly be taken to include, but not be limited to, solid-state memories, and optical and magnetic media.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be in any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to include, "based at least in part on," such that an un-recited feature or element is also permissible.

Some portions of the detailed descriptions are presented in terms of algorithms and symbolic representations of operations on data bits within a computer memory. These algorithmic descriptions and representations are the means used by those skilled in the video processing arts to most effectively convey the substance of their work to others skilled in the art. An algorithm is here, and generally, conceived to be a self-consistent sequence of steps leading to a desired result. The steps are those requiring physical manipulations of physical quantities.

It should be borne in mind, however, that all of these and similar terms are to be associated with the appropriate physical quantities and are merely convenient labels applied to these quantities. Unless specifically stated otherwise, as apparent from the above discussion, it is appreciated that throughout the description, discussions utilizing terms such as "receiving", "providing", "transmitting", "determining", "generating", "executing", or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Examples described herein also relate to an apparatus for performing the methods described herein. This apparatus may be specially constructed for performing the methods described herein, or it may comprise a general-purpose computer system selectively programmed by a computer program stored in the computer system. Such a computer program may be stored in a computer-readable tangible storage medium.

The methods and illustrative examples described herein are not inherently related to any particular computer or other apparatus. Various general purpose systems may be used in accordance with the teachings described herein, or it may prove convenient to construct more specialized apparatus to perform methods 300 and 400 and/or each of its individual functions, routines, subroutines, or operations. Examples of the structure for a variety of these systems are set forth in the description above.

Whereas many alterations and modifications of the disclosure will no doubt become apparent to a person of ordinary skill in the art after having read the foregoing description, it is to be understood that any particular implementation shown and described by way of illustration is in no way intended to be considered limiting. Therefore, references to details of various implementations are not intended to limit the scope of the claims, which in themselves recite only those features regarded as the disclosure.

What is claimed is:

1. A device, comprising:
    a cubicle comprising a first opening and a second opening, and a cavity disposed therein, wherein the first opening is opposite the second opening and the second opening is adapted to receive an item to be disposed into the cavity, the item corresponding to an order associated with an order identifier (ID);
    a sensor coupled to the cubicle to detect a state of the item with respect to the cavity, wherein the state of the item comprising at least a presence of the item detected, via the sensor, in the cavity of the cubicle; and
    an access assembly coupled to the first opening and the sensor, the access assembly adapted to:
        receive instructions to activate, from a scanning station communicably coupled to a group of cubicle devices comprising the cubicle, the instructions provided by the scanning station in response to receipt of the order ID to cause access to the cubicle; and
        wirelessly activate, responsive to the received instructions and responsive to the state of the item comprising the presence of the item detected in the cavity, to provide authenticated access via the first opening to the item in the cavity based on the state of the item.

2. The device of claim 1, wherein the state of the item further comprises detecting, via the sensor, a removal of the item from the cavity of the cubicle.

3. The device of claim 1, further comprising a user-perceivable indicator coupled to the cubicle, wherein the user-perceivable indicator indicates an association between the cubicle and a user based on the state of the item.

4. The device of claim 3, wherein the user-perceivable indicator comprises a digital faceplate to generate a graphic to indicate to the user that the item is stored in the cubicle.

5. The device of claim 1, further comprising a door assembly coupled to the first opening of the cubicle, wherein the access assembly is further adapted to activate the door assembly based on a scan of an identifier provided by a user device.

6. The device of claim 5, wherein the access assembly is adapted to activate the door assembly based on proximity of the user device associated with the item to the cubicle.

7. The device of claim 1, further comprising a light system coupled to the cubicle to periodically sanitize an interior of the cubicle.

8. The device of claim 1, further comprising an interlocking system coupled to the cubicle to secure a portion of the cubicle to at least one other cubicle.

9. A system comprising:
    a group of cubicle devices; and
    a scanning station communicatively coupled to the group of cubicle devices, the scanning station comprising a processing device to:
        detect that a user device associated with a request for an item is within a threshold range of the scanning station, the item corresponding to an order associated with an order identifier (ID);

identify a state of the item with respect to an interior cavity of at least one cubicle device of the group of cubicle devices based on a sensor of the at least one cubicle device, wherein the state of the item comprising at least a presence of the item detected, via the sensor, in the cavity of the cubicle;

send instructions to activate to the at least one cubicle device, the instructions provided by the scanning station in response to receipt of the order ID to cause access to the cubicle; and cause, responsive to the instructions and responsive to the state of the item comprising the presence of the item detected in the cavity, an access assembly of the at least one cubicle device to activate to provide authenticated access to the interior cavity based on the state of the item.

10. The system of claim 9, wherein the state of the item further comprises a removal of the item from the cavity of the cubicle.

11. The system of claim 9, wherein the processing device is further to activate a user-perceivable indicator to indicate an association between the at least one cubicle device and a user of the user device.

12. The system of claim 9, wherein the processing device is further to:

compare a first identifier associated with the item with a second identifier presented by the user device at the scanning station; and actuate an access assembly at a first opening of the at least one cubicle device based on a match between the first identifier and the second identifier.

13. The system of claim 12, wherein the processing device is further to actuate the access assembly based on proximity of the user device to the at least one cubicle device.

14. The system of claim 9, wherein the processing device is further to:

detect removal of the item from the at least one cubicle device based on the sensor; and active a light system to sanitize an interior of the at least one cubicle device.

15. The system of claim 9, further comprising:

a reader device electronically coupled to the group of cubicle devices, wherein the reader device is adapted to receive an identifier associated with the item that activates an indicator on at least one cubicle device of the group indicating the item is to be placed therein.

16. A non-transitory computer-readable medium comprising executable instructions that, when executed by a processing device, cause the processing device to:

detect, by the processing device, that a user device associated with a request for an item is within a threshold range of a scanning station communicatively coupled to a group of cubicle devices, the item corresponding to an order associated with an order ID;

identify a state of the item with respect to an interior cavity of at least one cubicle device of the group of cubicle devices based on a sensor of the at least one cubicle device, wherein the state of the item comprising at least a presence of the item detected, via the sensor, in the cavity of the cubicle;

receive instructions to activate, from the scanning station, the instructions provided by the scanning station in response to receipt of the order ID to cause access to the cubicle; and activate, responsive to the received instructions and responsive to the state of the item comprising the presence of the item detected in the cavity, the at least one cubicle device to provide authenticated access to the interior cavity based on the state of the item.

17. The non-transitory computer-readable medium of claim 16, wherein the state of the item further comprises a removal of the item from the cavity of the cubicle.

18. The non-transitory computer-readable medium of claim 16, wherein the processing device is further to activate a user-perceivable indicator to indicate an association between the at least one cubicle device and a user of the user device.

19. The non-transitory computer-readable medium of claim 16, wherein the processing device is further to:

compare a first identifier associated with the item with a second identifier presented by the user device at the scanning station; and actuate an access assembly at a first opening of the at least one cubicle device based on a match between the first identifier and the second identifier.

20. The non-transitory computer-readable medium of claim 19, wherein the processing device is further to actuate the access assembly based on proximity of the user device to the at least one cubicle device.

* * * * *